(12) United States Patent
Brass (10) Patent No.: US 7,145,649 B2
(45) Date of Patent: Dec. 5, 2006

(54) METHOD OF PRODUCING AN ULTRA-VIOLET OR NEAR ULTRA-VIOLET LIGHT SOURCE FOR NON-DESTRUCTIVE INSPECTION OR TESTING

(75) Inventor: Jack Brass, Toronto (CA)

(73) Assignee: Brasscorp Limited (CA)

( * ) Notice: Subject to any disclaimer, the term of this patent is extended or adjusted under 35 U.S.C. 154(b) by 0 days.

(21) Appl. No.: 10/021,574

(22) Filed: Dec. 19, 2001

(65) Prior Publication Data

US 2002/0093649 A1    Jul. 18, 2002

Related U.S. Application Data

(60) Provisional application No. 60/256,965, filed on Dec. 21, 2000.

(51) Int. Cl.
*G01N 21/00* (2006.01)
*G02B 5/00* (2006.01)

(52) U.S. Cl. ............... 356/237.1; 250/504 H (58) Field of Classification Search ........... 250/302, 250/492.2, 504 R, 504 H, 493.1; 356/237.1, 356/237.2–237.5, 51; 362/157, 171–178, 362/183–185, 198, 208, 230
See application file for complete search history.

(56) References Cited

U.S. PATENT DOCUMENTS

| | | | |
|---|---|---|---|
| 3,808,434 A * | 4/1974 | Gutbier ............... | 250/302 |
| 4,185,891 A | 1/1980 | Kaestner | |
| 4,826,269 A | 5/1989 | Harnagel et al. | |
| 4,935,665 A | 6/1990 | Murata | |
| 4,963,798 A | 10/1990 | McDermott ........... | 315/312 |
| 5,092,331 A | 3/1992 | Nakamura et al. ...... | 128/634 |
| 5,289,082 A | 2/1994 | Komoto | |
| 5,749,830 A | 5/1998 | Kaneko et al. ......... | 600/160 |
| 5,806,961 A | 9/1998 | Dalton et al. | |
| 5,954,206 A | 9/1999 | Mallon et al. ......... | 209/580 |
| 5,975,712 A | 11/1999 | Shiao | |
| 5,984,861 A | 11/1999 | Crowley ............... | 600/175 |
| 6,095,661 A * | 8/2000 | Lebens et al. ......... | 362/184 |
| 6,142,650 A | 11/2000 | Brown et al. | |
| D434,868 S | 12/2000 | Trigiani ............... | D26/45 |
| 6,165,384 A * | 12/2000 | Cooper et al. ......... | 252/301.19 |

(Continued)

FOREIGN PATENT DOCUMENTS

CA    2200364    5/1997

(Continued)

OTHER PUBLICATIONS

Craig Johnson, LEDTronics FlashLED, The LED Museum, pre-Sep. 4, 2000, http://ledmuseum.home.att.net/tronics.htm

(Continued)

*Primary Examiner*—Gregory J. Toatley, Jr.
*Assistant Examiner*—Juan D. Valentin, II
(74) *Attorney, Agent, or Firm*—Katten Muchin Rosenman LLP (57) ABSTRACT

There is provided an apparatus having at least one LED capable of emitting near ultraviolet or ultraviolet radiation to excite a luminescent material for non-destructive fault testing. The radiation may also be focused using a lens. There is also provided a method for detecting a fault in a body, comprising the steps of applying a luminescent material to the body in a manner to concentrate the luminescent material in a pattern indicative of the location of a fault in the body; activating an LED to emit ultraviolet radiation; shining the radiation transmitted from the LED onto the body to excite the luminescent material; and detecting a fault by the fluorescence of the luminescent material indicative of the location of the fault in the body.

22 Claims, 3 Drawing Sheets

U.S. PATENT DOCUMENTS

| | | | |
|---|---|---|---|
| 6,183,086 B1 | 2/2001 | Neubert | |
| 6,200,134 B1 | 3/2001 | Kovac et al. | |
| 6,250,771 B1 | 6/2001 | Sharrah et al. | 362/184 |
| 6,305,818 B1 * | 10/2001 | Lebens et al. | 362/184 |
| 6,357,893 B1 * | 3/2002 | Belliveau | 362/285 |
| 6,468,077 B1 | 10/2002 | Melikechi et al. | 433/29 |
| 6,485,160 B1 | 11/2002 | Sommers et al. | |
| 6,491,408 B1 | 12/2002 | Cooper et al. | |
| 6,590,220 B1 * | 7/2003 | Kalley et al. | 250/504 H |
| 6,710,363 B1 | 3/2004 | Trigiani | 250/504 H |
| 2002/0191396 A1 | 12/2002 | Reiff et al. | 362/246 |
| 2003/0007345 A1 * | 1/2003 | Cooper et al. | 362/139 |
| 2003/0007346 A1 * | 1/2003 | Cooper et al. | 362/184 |
| 2003/0098425 A1 | 5/2003 | Sosinsky | 250/504 R |
| 2003/0123254 A1 | 7/2003 | Brass et al. | |
| 2003/0142489 A1 * | 7/2003 | Cooper et al. | 362/109 |

FOREIGN PATENT DOCUMENTS

| | | |
|---|---|---|
| CA | 2200365 | 5/1997 |
| CA | 2284870 | 9/1998 |
| CA | 2280398 | 4/2000 |
| CA | 2405802 | 10/2001 |
| DE | 25 42 220 A | 3/1977 |
| DE | 299 574 A5 | 4/1992 |
| DE | 20021934 U1 | 5/2001 |
| DE | 201 10 813 | 10/2001 |
| EP | 0 523 927 A2 | 1/1993 |
| EP | 1 059 202 A2 | 12/2000 |
| GB | 810256 | 3/1959 |
| WO | WO 98/39636 | 9/1998 |
| WO | WO 99/35486 | 7/1999 |
| WO | WO 01 52605 A2 | 7/2001 |
| WO | WO 01 81973 A1 | 11/2001 |
| WO | WO 03/004932 | 1/2003 |
| WO | WO 03/025458 A1 | 3/2003 |

OTHER PUBLICATIONS

Hi-Power FlashLED® Flashlights, LEDTronics, Inc., date unknown, http://www.netdisty.net/ds/flt-3001/default.asp.

Osram Sylvania, Preliminary data sheet for OS-WL01A, Dated Feb. 25, 2000.

LED Museum at http://ledmuseum.home.att.net/ledleft.htm printed Feb. 27, 2002.

Product pages for Dorcy "Cool Blue" at http://www.dorcy.com/led%20new.htm printed Feb. 27, 2002.

Saftey LED Hi-Power FlashLED Flashlights at http://secure.implex.net/NBAComputers/browse.cfm?CategoryID=8 printed Dec. 10, 2001.

Review of LEDTronics Mini-FlashLED at http://ledmuseum.home.att.net/flashled.htm printed Dec. 10, 2001.

M. Sayer, et al., "Measurement, Instrumentation and Experiment Design in Physics and Engineering," Prentice-Hall of India, New Delhi, (2000), pp. 197-198 (ISBN 81-203-1269-4).

L. R. Koller, "Ultraviolet Radiation," (2nd Ed.), John Wiley & Sons, New York, (1965), pp. 158-181.

\* cited by examiner

METHOD OF PRODUCING AN ULTRA-VIOLET OR NEAR ULTRA-VIOLET LIGHT SOURCE FOR NON-DESTRUCTIVE INSPECTION OR TESTING

This application claims priority benefit from U.S. Patent Application No. 60/256,965, filed Dec. 21, 2000.

FIELD OF THE INVENTION

The invention relates to methods and apparatus for locating faults in an object, system or components thereof. In particular, the invention relates to using light sources and dyes to locate faults in machinery.

BACKGROUND OF THE INVENTION

Luminescent materials are often used to detect faults, such as leaks or stress fractures. Such luminescent materials can be applied to a body in many ways. Two common ways include using magnetic particles and liquid penetrants.

Magnetic particles such as iron filings are mixed with fluorescent materials and applied to a body. The particles and fluorescent materials form distinctive patterns depending upon the characteristics of the body. For example, fluorescent dyes combined with iron filings can be used to detect faults such as stress fractures. The fluorescent material is applied to a body to be tested in such a way as to highlight a fault in the body when the material is illuminated by shining a lamp emitting light of a particular wavelength on the body. The combined iron filings and fluorescent dye are attracted to the fault and the dye emits visible light when illuminated by incident light of an appropriate wavelength. For example, metal in aircraft components will act differently in the presence of magnetic fields and thus cause distinctive patterns of magnetic particles applied to the components, depending upon the existence of faults within the components. Such faults are typically caused by previous stresses.

Liquid penetrants are also mixed with fluorescent materials to reveal faults by penetrating cracks or other faults in a body. For example, a luminescent material in the nature of a fluorescent dye is injected or poured into a component or system. Where a leak occurs the dye may escape from the system. Shining a light of appropriate wavelength (typically ultraviolet or near ultraviolet) on the system will cause the dye to fluoresce in the area of the leak. The existence and location of a leak or leaks are then evident.

Leaks in various liquid and vapor circulating systems, such as air conditioners, may be discovered by including a dye with the circulating liquid or vapor. The dye used is preferably capable of fluorescing when exposed to an ultraviolet or near ultraviolet ("UV") spot light or flood light. These lights typically emit light having a wavelength in the 385 to 485 nanometer range. As described above, leaks may be detected by illuminating the system with such a light to fluoresce any dye escaping from the system. The dye may be injected, poured or otherwise introduced into the system. A leak may be detected as the liquid or vapor, which includes a fluorescing dye, escapes from the system or apparatus, for example, through a hole or crack, or at a seal or other connection that is failing. The fluorescence of the dye may then be detected by visual inspection using the near UV spot light or flood light to cause the dye to fluoresce.

Typically, light energy or radiation that has its peak output in a wavelength range of 385 to 465 nanometers will cause a luminescent material such as a fluorescent dye to fluoresce. Light falling outside of this range may tend to interfere with detection of the fluorescing dye. Accordingly, to improve detection, it may be preferable to reduce the presence of any remaining visible light, which typically has a wavelength in the 480 and 700 nanometer range. Reduction of interfering visible light may be achieved by placing a filter in the path of the emitted light.

Near UV spot lights or flood lights typically contain incandescent lamps, such as tungsten halogen lamps, along with a filter which inhibits transmission of light energy (or radiation) outside of the 385 to 465 nanometer range. These lights may be flashlight or lantern type devices that emit a beam of near UV energy. They can operate while powered by a self-contained battery or an electrical outlet. The incandescent light source, however, is not generally considered to be an efficient means of producing near UV energy because over 80% of the energy is typically emitted as infrared light or heat, and only about one percent of the energy emitted is near UV energy. A usable beam of energy is obtained because these lamps produce a narrow, intense beam of light from a "point source" (i.e., the energy emits from a concentrated area of the light source).

When a flood light for close inspection is desired, a black light blue ("BLB") type fluorescent lamp whose energy output is limited to the near UV range may be used. A miniature or compact version of such a lamp may be convenient for close inspection of difficult to access parts of the system being inspected. It is desirable to be able to bring the lamp in to close proximity with the fault. This is often difficult to achieve, even with miniature versions of such fluorescent lamps, when used in the tight spaces typically available when working around machinery and equipment.

Use of fluorescent lamps generally reduces the need for a filter to reduce the visible light emitted. Since these lamps are "area sources" (i.e., the energy emits from a relatively large area of the light source) and not point sources, they can generally only produce a floodlight beam which can be difficult to focus on a particular area of an inspected system. In particular, fluorescent lamps tend to generate a low intensity of incident ultraviolet radiation. However, they are generally advantageous in that they can efficiently produce near UV energy. Typical lamps are 4 to 13 watts and they can operate using a ballast powered by batteries or line voltage.

Based on the foregoing, alternative methods and apparatus for using lamps and dyes to locate faults and defects in machinery and other equipment is desirable.

SUMMARY OF THE INVENTION

The invention consists of an apparatus for use with a body to be tested for faults using a luminescent material. According to one broad aspect of the invention, the apparatus includes comprising at least one LED capable of emitting radiation to excite the luminescent material, and a power supply connected to the at least one LED to provide the LED with electricity.

In an illustrative embodiment of the invention the radiation emitted by the LED includes either near ultraviolet or ultraviolet radiation or both.

In a yet further illustrative embodiment of the invention, the apparatus includes a housing having an open end, wherein the at least one LED is attached to a substrate and is mounted within the housing adjacent the open end, and the LED is oriented to emit radiation through the open end.

According to another broad aspect of the invention, there is provided a method for detecting a fault in a body, including the steps of applying a luminescent material to the body in a manner to concentrate the luminescent material in a pattern indicative of the location of a fault in the body; activating an LED to emit ultraviolet radiation; shining the radiation transmitted from the LED onto the body to excite the luminescent material; and detecting a fault by the fluorescence of the luminescent material indicative of the location of the fault in the body.

In an illustrative embodiment of the invention a plurality of LEDs arranged in an array are activated to emit radiation having a wavelength in the range of 385 to 465 nanometers.

According to a further broad aspect of the invention, there is provided a method of using an LED for detecting a fault in a body, comprising applying a luminescent material to the body in a manner to concentrate the luminescent material in a pattern indicative of the location of a fault in the body; activating the LED to emit radiation; shining at least a portion of the radiation emitted from the LED onto the body to excite the luminescent material; and detecting a fault by the fluorescence of the luminescent material indicative of the location of the fault in the body.

In an illustrative embodiment of the invention the radiation is near ultraviolet radiation.

According to another broad aspect of the invention, there is provided a use of at least one LED capable of emitting radiation to excite a luminescent material for non-destructive fault testing.

According to another broad aspect of the invention, there is provided a kit having a lamp including at least one LED housed within the lamp, the LED being capable of generating ultraviolet radiation; and a luminescent material capable of absorbing at least a portion of the radiation, converting the radiation to energy, and emitting the radiation at a visible wavelength.

In an illustrative embodiment of the invention the lamp is a handheld lamp and the LED emits ultraviolet radiation in the range of 385 to 465 nonometers.

BRIEF DESCRIPTION OF THE DRAWINGS

For a better understanding of the present invention and to show more clearly how it may be carried into effect, reference is now made, by way of example and not of limitation, to the accompanying drawings in which.

DETAILED DESCRIPTION OF THE INVENTION

The description that follows, and the embodiments described therein, are provided by way of illustration of an example, or examples of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated in order more clearly to depict certain features of the invention.

Figure 1:
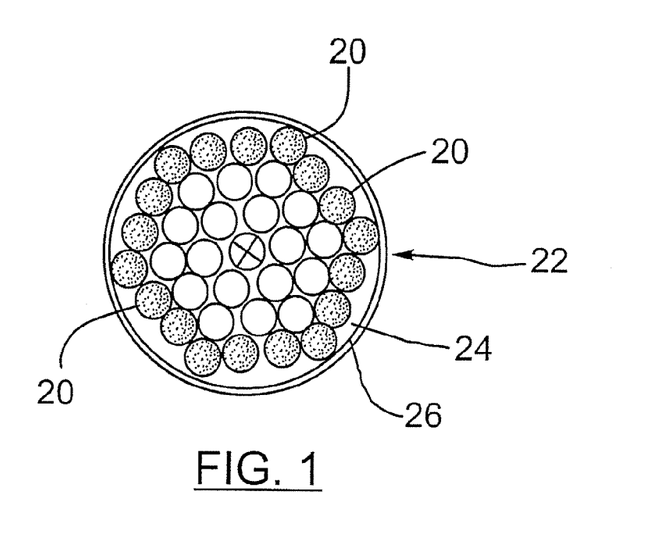
FIG. 1 is a plan view of an array of LEDs of the present invention.

Referring to FIG. 1, a preferred embodiment of the apparatus of the present invention includes a light-emitting diode 20 ("LED"). LED 20 emits radiation (or light) to cause a chosen luminescent material, such as a fluorescing dye, to emit visible radiation at a substantially different wavelength or range of wavelengths when illuminated by incident rays of light from LED 20.

LED 20 is a relatively efficient light source. Depending on their configuration, LEDs can emit light of various wavelengths from the visible spectrum including red, green and yellow. LEDs generally have a relatively rugged construction and a relatively small, intense area of energy emission. The LEDs tend to have a limited bandwidth, making them suited for the demands of non-destructive inspection or testing. LEDs also tend to have a relatively longer useful life than other light sources, such as those described above. LEDs have been used in traffic signals where an array of LEDs provides a long life red, green or yellow signal. A high intensity blue LED has been developed for generally high technology applications. For example, blue LEDs are used for large area picture display panels where the combination of the primary color red, blue and green LEDs can be varied in intensity to provide pictures or words in full color.

In this description the term "luminescent materials" is used to describe materials that are stimulated or excited by incident radiation having a wavelength typically in the ultraviolet range. When stimulated, such materials emit light in the visible range and then return to their original state. In most cases the emitted radiation has a substantially different wavelength than the incident radiation. The wavelengths are substantially different in the sense that an unaided eye can distinguish the different wavelengths. Where the incident wavelength from the energy source is invisible, or barely visible, ultraviolet light, and the wavelength emitted from the luminescent material is visible light, then the wavelengths will be substantially different and the presence of the luminescent material may tend to be detectable by an unaided eye.

In this description, luminescent materials include both fluorescent and phosphorescent materials. Fluorescent materials typically emit radiation within about $10^{-8}$ seconds after being stimulated, while phosphorescent materials emit within longer periods of up to hundredths of seconds. Luminescent materials are normally solids that are typically dissolved in solvents to create a solution for use in locating faults.

When connected to a power source (described below), LED 20 emits radiation in the violet and deep blue wavelengths. Like other LEDs, LED 20 is a relatively efficient device for emitting a beam of near UV energy from an intense point source as compared to other light sources such as spot lights or flood lights. LED 20 preferably has an output in the 385 to 465 nanometer wavelength range to produce near UV energy that is capable of exciting or fluorescing dyes used for liquid and/or vapor leak detection. The radiant energy emitted by LED 20 is generally limited to this range with little or no radiant energy emitted outside of this relatively narrow bandwidth.

The intensity of LEDs generally tends to be greater than other light sources, however, the total power of the LED is relatively low, which can limit the distance that the beam from a single LED is projected. To attempt to ameliorate this, a cluster or array 22 of LEDs 20, as seen in FIG. 1, combine to emit a light beam that may be projected a greater distance, and that may illuminate a greater area, than a single LED 20. LEDs are available with an output of emitted radiation covering an arc of between about 20 and 180 degrees. The emitted radiation typically has a generally conical shape, particularly when the arc is less than 180 degrees. The narrow beam LEDs (e.g., 20 degrees) have the greatest directional intensity and therefore provide the greatest potential for use in an array of LEDs for use in leak detection. LEDs 20 of the preferred embodiment have a diameter of about 6.6 millimeters and a narrow beam output.

LEDs in general tend to have the following advantages over other devices that are used for producing beams of energy: they tend to have a longer operational life span, they are capable of emitting a high intensity beam of energy having a point source, and they are generally more rugged in construction. Accordingly, LEDs 20 may be advantageously used for leak detection because they can be placed in physically demanding conditions. For example, LEDs 20 may be subject to high temperatures and humidity levels, and may be knocked about when positioned adjacent to possible leak sites.

As shown in FIG. 1, LEDs 20 are arranged on a support or substrate such as a circuit board 24. To maintain a generally uniform and concentrated beam of energy, LEDs 20 are preferably located adjacent one another on the same side 26 of circuit board 24. While array 22 is shown in FIG. 1 as having staggered rows of LEDs 20 in a generally hexagonal pattern, other arrangements may also be used depending on the requirements of a particular testing or inspection task. For example, if a wider beam of energy is required, LEDs 20 may be spaced apart from one another as an alternative (or in addition to) using wide beam LEDs. Such an arrangement may reduce the combined intensity of any beam of energy emitted. Accordingly, additional LEDs 20 may be added to increase the area of array 22 and to increase beam intensity.

In the preferred embodiment, array 22 has 36 LEDs 20 arranged to cover a generally circular area having a diameter of about two inches. As shown in FIG. 1, array 22 does not have an LED 20 at its centre. This is done merely for convenience in the arrangement of LEDs 20. An additional LED 20 may be added (indeed LEDs 20 may be added to or remove from array 22 depending on the particular requirements of a given testing or inspection task). The described arrangement of LEDs 20 provides a relatively concentrated beam of energy suitable for non-destructive leak detection and other testing using luminescent materials. LEDs 20 may be alternatively positioned in other arrangements depending on the configuration of the system or component being inspected. For example, two or more LEDs 20 could be arranged linearly for insertion into a narrow opening to illuminate the inside thereof. The number of LEDs 20 used may also be increased or decreased depending on the size, shape or configuration of the component or system being examined.

Figure 2:
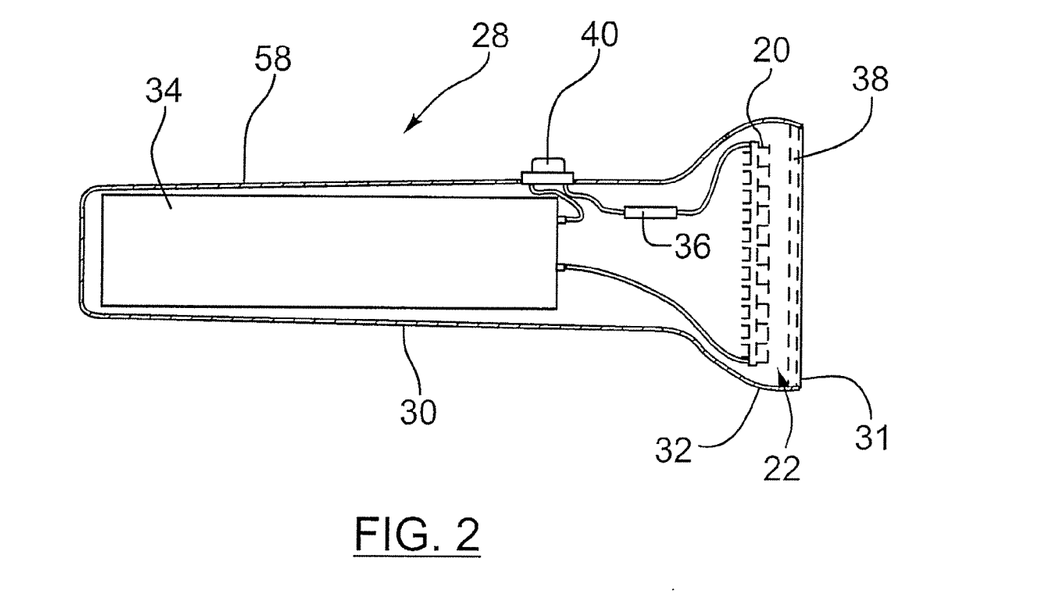
FIG. 2 is a transparent side view of a flashlight housing the array of LEDs of FIG. 1.

Referring to FIG. 2, the size of any device used for leak detection is preferably relatively small. Larger devices may tend to be relatively more difficult to position to illuminate components or sub-components of a machine or other system being inspected for leaks. As shown in FIG. 2, a lamp such as a hand held flashlight 28 may be conveniently used to house array 22 of LEDs 20 for use in leak detection. Flashlight 28 may be readily positioned to illuminate small and/or difficult to reach areas of a machine or system being inspected. Using an array 22 having approximately 36 LEDs 20 will tend to have a maximum operative limit of approximately 2 feet from the area being inspected. Positioning flashlight 28 any further away from the inspected area may reduce that ability of the array 22 to adequately fluoresce any dye present at a leak or fault site.

Flashlight 28 has a housing 30 that contains a power source (such as one or more batteries, not shown) and array 22. Array 22 is preferably oriented so that it may be positioned at an open end 31 of housing 30 to radiate a beam of energy at an angle generally perpendicular to the surface of an area being inspected. This may tend to cause the amount of incident radiation at a potential leak site to approach a maximum value. Accordingly, energy emitted from LEDs 20 is preferably substantially unobstructed by flashlight housing 30. A protector in the nature of a substantially transparent shield 38 may be mounted to housing 30 between LEDs 20 and the inspected area. Shield 38, to some extent, protects LEDs 20 from the environment in which it operates while permitting the beam of energy produced by LEDs 20 to pass therethrough. In some circumstances, a basic shield such as a mesh, grate, or other protective material (not shown), may be used instead of, or in addition to, shield 38. Shield 40 may be clear or may even made from a wire mesh or protective material, as long as it is transmissive in the desired near ultraviolet or ultraviolet wavelengths, as appropriate. In the present embodiment, shield 40 is provided primarily to protect the LEDs 20 from damage and to keep the LEDs 20 clean.

LEDs 20 operate on direct current which permits them to be powered using line voltage, a battery 34 or some other power source. LEDs 20 may be connected to a power source such as battery 34 in any manner known in the art that generally satisfies the requirements described herein. Power to LEDs 20 may be activated by a switch 40 that controls the flow of energy from the power source (e.g., battery 34) to LEDs 20. Typical voltages for LEDs 20 are 2 to 6 volts with an operating current per LED element of 0.02 to 0.06 amps. Accordingly, an array 22 of LEDs 20 generally has power load requirements similar to common handheld flashlights and lanterns having, for example, tungsten light bulbs. A resistor may be included in the connection between the power source 34 and array 22 to reduce the amount of energy received by array 22 thereby increasing the effective life span of LEDs 20.

Figure 3:
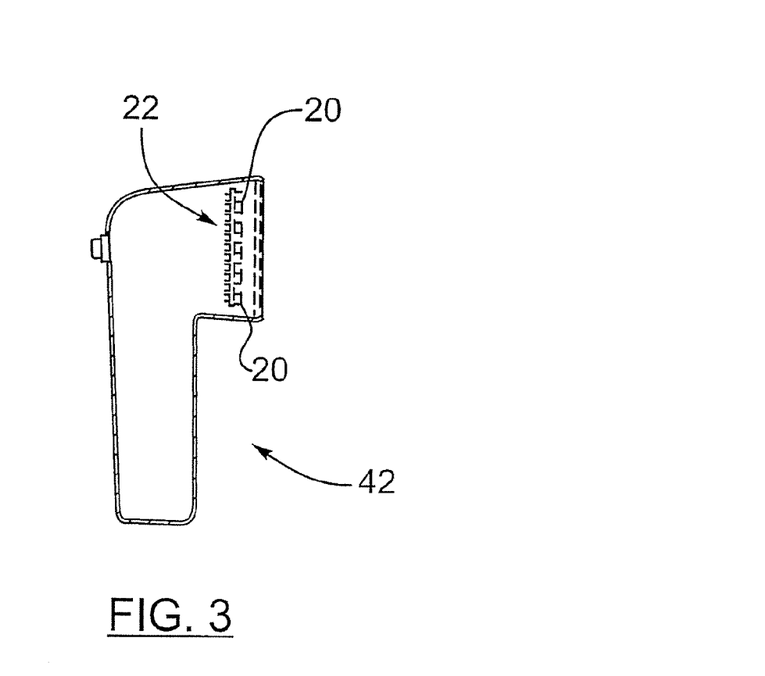
FIG. 3 is a side view of an alternative flashlight for housing the LEDs of FIG. 1.

Referring to FIG. 3, an alternate flashlight 42 configured to house and activate LED array 22 is shown. Flashlight 42 may be easier to hold than flashlight 28, and may permit access to different locations, where the ability to shine sideways is important. Flashlight 42 may also be provided with a swivel head (not shown) so that radiation may be directed at different angles relative to the body of flashlight 42.

Figure 4:
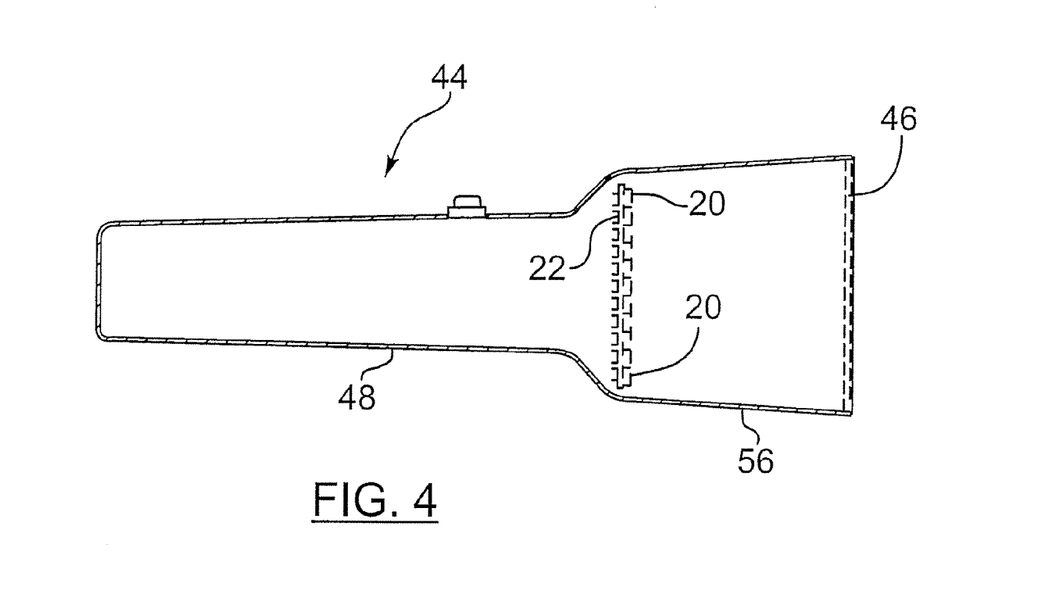
FIG. 4 is a transparent side view of a yet further alternative flashlight for housing the LEDs of FIG. 1.

Referring to FIG. 4, where inspection is done at a greater distance than described above (e.g., at greater than about two feet from the area to be inspected), an alternatively configured flashlight 28, shown as 44 in FIG. 4, may include a lens 46. Lens 46 is preferably in spaced relationship with LED array 22, and replaces or augments shield 38. The spaced relationship between lens 46 and array 22 permits the focusing of energy emitted from LEDs 20 to an area being inspected. Lenses of different sizes and shapes may be used depending on the particular requirements for the inspection task. In the preferred embodiment, a Fresnel lens 46 is used.

Figure 5:
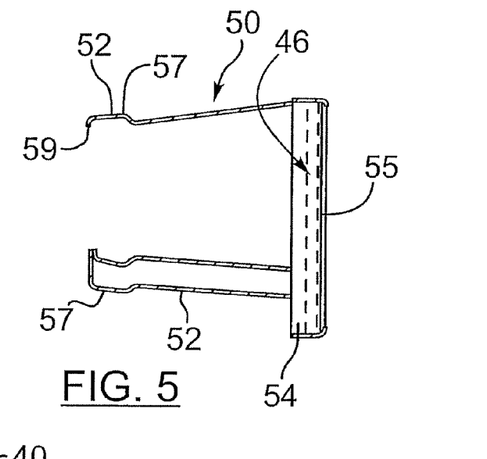
FIG. 5 is a side view of a clip-on device for use in conjunction with the flashlight of FIG. 4.

Lens 46 may be permanently or semi-permanently mounted to housing 48 of flashlight 44. Alternatively, lens 46 may be conveniently removably mounted to housing 48 as part of a clip-on device 50, as shown in FIG. 5. Clip-on 50 may have two or more resilient arms 52 spaced generally equidistant from one another and projecting generally proud of a retaining rim 54. Retaining rim 54 receives a ring 55 for retaining lens 48 and arms 52. Arms 52 co-operate to receive and bias against a periphery of flashlight housing extension 56 to frictionally retain lens 48 to flashlight 44. To increase the friction between an arm 52 and housing extension 56, each arm 52 may have a feature in the nature of a hump 57. Hump 57 causes a free end 59 of at least one arm 52 to be oriented for contact with housing extension 56 at a point or a line of contact. This reduced area of contact serves to increase the friction between arm 52 and housing extension 56. Each resilient arm 52 is preferably hingedly connected at an end to ring 55 to permit each arm 52 to be rotated towards lens 46 and to lie adjacent lens 46 for storage. In the embodiment shown, flashlight 44 having lens 48, projects a usable beam for a distance of approximately 5 to 10 feet, depending on variables such as the number of LEDs 20 used, the voltage applied to the LEDs 20, and the characteristics of the lens 48. Lens 48 may also be adjustably mounted, for example by threaded connection, to flashlight 44 (not shown) so that the focal length of a beam emitted by LEDs 20 may be varied.

The Violet Laser Diode developed by the Nichia Corporation of Tokyo, Japan (the "Nichia LED") may be used for LED 20. The Nichia LED appears to have been developed for uses including use as a white light LED (which is achieved by adding phosphor to the LED), and use in next generation DVD players that play movies and read data from DVD-ROM media. The wavelength emitted from the Nichia LED is claimed to provide a fivefold increase in the storage capacity of DVDs. The Nichia LED produces a significant portion of its energy in a one nanometer wavelength bandwidth centered typically at 405 nanometers. However, this wavelength can vary from 395 to 415 nanometers. Since this band has a wavelength that is centered in the desired range of energy needed to excite a fluorescent dye, it is suited for use in the preferred embodiment of the invention. The Nichia LED is also preferred in that it has a beam that is relatively concentrated, having a 20 to 30 degree width. If the Nichia LED is used, each LED 20 in an array 22 will consume approximately 0.2 watts, and an array of 36 LEDs 20 would consume approximately 7.2 watts. This energy input is sufficient to produce the desired near UV energy for non-destructive testing. In contrast, in the prior art, a 50 watt incandescent lamp with a filter is required, and only about one percent of the output energy is near UV energy. Embodiments of the present invention do not require a light filter when used for non-destructive testing as described herein.

Other LEDs that emit energy in the desired near UV energy band are, or will soon be, available in the marketplace. The high intensity, rugged construction and long life of an LED, such as the Nichia LED, makes it suited to leak inspection.

Figure 6:
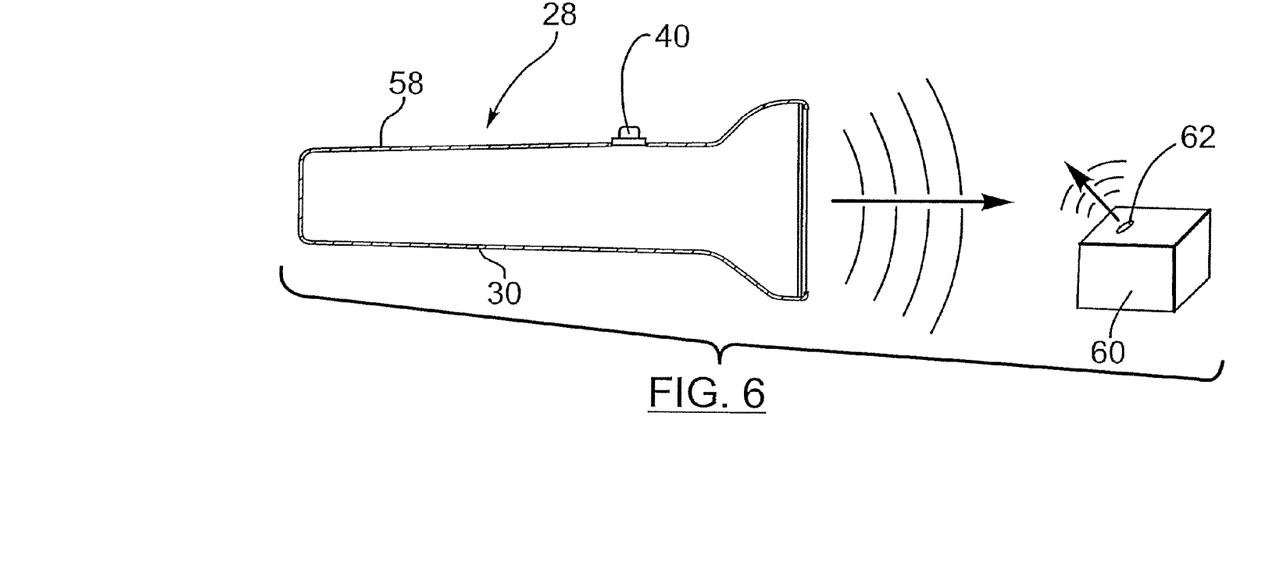
FIG. 6 is a side view of the flashlight of FIG. 2 irradiating an object to fluoresce a dye emanating therefrom.

Referring to FIG. 6, an example of the operation of flashlight 28 follows. Operation of the other embodiments 42 and 44 is similar. Luminescent material 62, typically in the form of a dye, is provided, and is applied to an object or body 60 for which leak detection is desired. For example, in a cooling system, hydraulic system, or other type of fluid carrying system the die may be applied internally, as by injection, and then the system may be pressurized, thereby tending to cause the luminescent die to leak. Alternatively, as when seeking stress corrosion or fatigue cracks, a luminescent die mixture may be applied to a surface with a brush or cloth, or spray device, and the excess wiped off, as needed.

To operate flashlight 28, an operator grips handle portion 58 of flashlight housing 30 and aims the LEDs 20 at an object or body that is being tested, for example an automotive air conditioning component 60. Switch 40 is depressed and LEDs 20 of array 22 are provided with energy and emit light at a predetermined wavelength. Luminescent material 62 in solution that is leaking from a fault in the component 60 absorbs the incident light and emits visible radiation. The emitted radiation stands out to allow the operator to see it and to identify the fault. A similar procedure is used for testing other objects such as an aircraft wing (not shown). In the case of an aircraft wing, non-destructive testing is used to identify possible stress fractures or other such faults in the wing. Fluorescent dye mixed with magnetic particles produce a distinctive pattern in the area of the fault. Near ultraviolet, or ultraviolet light, as the case may be, from flashlight 28 causes the dye to fluoresce and reveal a pattern which identifies the location of the stress fracture or fault. An operator observing the luminescence may then tend to be able to locate the zone of interest, be it a leak, a crack, fault or other defect.

A resistor or resistors 36 having a lower impedance may be used to increase the voltage applied to LEDs 20. For example a 2.2 ohm resistor may be used instead of a 12 ohm resistor. A lower impedance enables a voltage that is greater than the nominal rating for the LEDs 20 to be applied. This increased voltage can increase the intensity of ultraviolet incident radiation for the same LED 20. The increase in intensity of ultraviolet radiation is often greater than the increase in the intensity of the visible wavelength radiation emitted from LED 20, if any. LEDs 20 may also be overdriven by eliminating resistor 36 altogether.

Increasing the voltage inputted to LEDs over their nominal rating (for example, by 25%) has been found to leave sufficient LED life, while significantly increasing the intensity of ultraviolet exciting or stimulating radiation. If each LED 20 is driven to output a greater amount of energy, then either fewer LEDs 20 are required for a given application, or a similar number of LEDs 20 are effective at a greater distance from an inspected object, or both.

Reduction in bulb life is due to the increased temperature at which LEDs 20 operate internally. The increased temperature can greatly reduce the life of the LEDs 20. However, given that the LEDs 20 are not generally activated for long periods, the reduction in the rated life of LEDs 20 may be less noticeable, and may not be noticeable at all. For example, LEDs may generally be expected to last for months, if not years, when in regular use. Accordingly, an LED with its life span reduced by being overdriven might still take a significant amount of time to fail when used for non-destructive testing in the manner practiced in the art. As a result, there might be no practical reduction in the life span of an LED 20 when overdriven as described above.

Each flashlight 28, 42 or 44 may be sold as a kit along with a luminescent material that matches the particular radiation incident from the flashlight 28, 42 or 44 and which is appropriate for a given application (for example, leak testing or testing for stress fractures). Alternatively, each flashlight 28, 42 or 44 may be sold separately from the corresponding luminescent material.

It will be understood by those skilled in the art that this description is made with reference to the illustrative embodiments and that it is possible to make other embodiments employing the principles of the invention which fall within its spirit and scope thereof. In particular, for some applications, LEDs 20 may be used to detect leaks or faults without LEDs 20 being embodied in the general form of a flashlight or other portable contrivance. Indeed, for some applications it may be appropriate that LEDs 20 be merely connected to an appropriate power source, whether portable or not, and directed to an area for inspection to detect the presence of any dye or other luminescent material that fluoresces when activated by energy emitted from LEDs 20. Such arrangements would not be appropriate where LEDs 20 require protection when in use (or when stored) or when portability is preferred or required.

What is claimed is:

1. A method for detecting a leak in a liquid or air circulating system, comprising the steps of:
    applying a fluorescent material to the system in a manner to cause the material to leak from the system;
    activating at least one LED in a handheld housing having an open end through which the radiation emits radiation, a substantial portion of the wavelength of radiation emitted from the at least one LED falling within a range from 395 to 415 nanometers, different from the fluorescent leak detection dye absorption peak wavelength, and wherein substantially less radiation is emitted from the at least one LED in wavelengths above 415 nanometers than is emitted within the range from 395 to 415 nanometers; and
    shining the radiation transmitted from the at least one LED onto the system to excite leaked fluorescent material; and
    detecting a leak by the fluorescence of the leaked fluorescent material.

2. The method of claim 1, further comprising the step of focusing said radiation emitted from said at least one LED using a lens.

3. The method of claim 1, wherein the beam angle of radiation emitted from each LED is less than or equal to 30 degrees.

4. The method of claim 1, further comprising the step of using a lens for focusing said radiation emitted by said LEDs.

5. The method of claim 1, further comprising the step of providing a usable beam of radiation for a distance 5 to 10 feet from said lens.

6. The method of claim 1, further comprising the step of providing a power supply in the handheld housing.

7. A kit comprising:
    (i) an inspection lamp for use in detecting leaks from a liquid or air circulating system using a fluorescent leak detection material, the lamp including:
    at least one LED capable of emitting radiation to produce fluorescence of the leak detection material that leaks from the system;
    a power supply connected to said at least one LED to provide said at least one LED with electricity, and wherein a substantial portion of the wavelength of radiation emitted from the at least one LED falls within a range from 395 to 415 nanometers, different from the fluorescent leak detection material absorption peak wavelength, and wherein substantially less radiation is emitted from the at least one LED in wavelengths above 415 nanometers than is emitted within the range from 395 to 415 nanometers; and
    a housing having an open end,
    wherein said at least one LED is attached to a substrate and is mounted within said housing adjacent the open end, and said at least one LED is oriented to emit radiation through the open end, and
    wherein the housing is handheld; and (ii) the fluorescent leak detection material being capable of absorbing at least a portion of the radiation emitted from the at least one LED, and fluorescing at a visible wavelength as a result.

8. The kit of claim 7, wherein the beam angle of radiation emitted from each LED is less than or equal to 30 degrees.

9. The kit of claim 7, further comprising a lens mounted to said open end for focusing said radiation emitted by said LEDs.

10. The kit of claim 9, wherein said lens provides a usable beam of radiation for a distance 5 to 10 feet from said lens.

11. The kit of claim 7, wherein said power supply comprises a battery and the housing is untethered.

12. A method for detecting a leak in a liquid or air circulating system, comprising the steps of:
    applying a fluorescent material to the system in a manner to cause the material to leak from the system;
    activating at least one LED in a handheld housing having an open end through which the radiation emits radiation, a substantial portion of the wavelength of radiation emitted from the at least one LED falling within a range from 395 to 415 nanometers, unmatched to the fluorescent leak detection dye absorption peak wavelength, and wherein substantially less radiation is emitted from the at least one LED in wavelengths above 415 nanometers than is emitted within the range from 395 to 415 nanometers; and
    shining the radiation transmitted from the at least one LED onto the system to excite leaked fluorescent material; and
    detecting a leak by the fluorescence of the leaked fluorescent material.

13. The method of claim 12, further comprising the step of focusing said radiation emitted from said at least one LED using a lens.

14. The method of claim 12, wherein the beam angle of radiation emitted from each LED is less than or equal to 30 degrees.

15. The method of claim 12, further comprising the step of using a lens for focusing said radiation emitted by said LEDs.

16. The method of claim 12, further comprising the step of providing a usable beam of radiation for a distance 5 to 10 feet from said lens.

17. The method of claim 12, further comprising the step of providing a power supply in the handheld housing.

18. A kit comprising:
    (i) an inspection lamp for use in detecting leaks from a liquid or air circulating system using a fluorescent leak detection dye, the lamp including:
    at least one LED capable of emitting radiation to produce fluorescence of leak detection dye that leaks from the system;
    a power supply connected to said at least one LED to provide said at least one LED with electricity, and wherein a substantial portion of the wavelength of radiation emitted from the at least one LED falls within a range from 395 to 415 nanometers, unmatched to the fluorescent leak detection dye absorption peak wavelength, and wherein substantially less radiation is emitted from the at least one LED in wavelengths above 415 nanometers than is emitted within the range from 395 to 415 nanometers; and
    a housing having an open end,
    wherein said at least one LED is attached to a substrate and is mounted within said housing adjacent the open end, and said at least one LED is oriented to emit radiation through the open end, and wherein the housing is handheld; and (ii) the fluorescent leak detection dye being capable of absorbing at least a portion of the radiation emitted from the at least one LED, and fluorescing at a visible wavelength as a result.

19. The kit of claim 18, wherein the beam angle of radiation emitted from each LED is less than or equal to 30 degrees.

20. The kit of claim 18, further comprising a lens mounted to said open end for focusing said radiation emitted by said LEDs.

21. The kit of claim 20, wherein said lens provides a usable beam of radiation for a distance 5 to 10 feet from said lens.

22. The kit of claim 18, wherein said power supply comprises a battery and the housing is untethered.

* * * * *